United States Patent [19]

Snapp, Jr.

[11] Patent Number: 4,759,760
[45] Date of Patent: Jul. 26, 1988

[54] CARDIOVASCULAR PUMP SYSTEM

[76] Inventor: Edward A. Snapp, Jr., 190 Lehmberg Rd., Columbus, Miss. 39702

[21] Appl. No.: 925,086

[22] Filed: Oct. 30, 1986

[51] Int. Cl.$^4$ .............................................. A61F 2/22
[52] U.S. Cl. .......................................................... 623/3
[58] Field of Search ....................................... 623/2, 3

[56] References Cited

U.S. PATENT DOCUMENTS 4,652,265 3/1987 McDougall .............................. 623/3

OTHER PUBLICATIONS

"Left Ventricular Assistance in Dogs Using a Skeletal Muscle Powered Device for Diastolic Augmentation", Nielsen et al, *Heart Transplantation*, vol. 4, #3, May 1985.
"Biomechanical Cardiac Assist Cardiomyoplasty and Muscle Powered Devices", R. C. J. Chic, chapter 12 (by Khalafalla), pp. 168-176, Sep. 1986.

*Primary Examiner*—Richard J. Apley
*Assistant Examiner*—James Prizant
*Attorney, Agent, or Firm*—Walker & McKenzie

[57] ABSTRACT

Structure and a method of implanting the structure to assist a patient's cardiovascular system in pumping blood from a vein to an artery. A chamber is associated with a vein and an artery to allow blood from the vein to flow thereinto. A length of living muscle is associated with the chamber in a manner that contraction of the muscle will cause at least a portion of the chamber to contract and pump blood therefrom into the artery.

8 Claims, 5 Drawing Sheets

CARDIOVASCULAR PUMP SYSTEM

BACKGROUND OF THE INVENTION

1. Field of the Invention

The present invention relates, in general, to cardiovascular pump systems and methods for pumping blood from a vein to an artery.

2. Description of the Related Art

A preliminary patentability search in Class 128, Subclass 1D and Class 623, Subclass 3 disclosed the following patents: Page et al, U.S. Pat. No. 3,827,426; Jarvik, U.S. Pat. No. 4,173,796; Runge, U.S. Pat. No. 4,302,854; and Robinson et al, U.S. Pat. No. 4,397,049. None of the above patents disclose or suggest the present invention. Page et al discloses a pump chamber formed out of a resilient material, such as silicone rubber, so as to simulate the interior and exterior contours of a ventricle of a heart with contractile elements formed of a Nitinol wire helically wound around the walls of the pump chamber so that the passage of electrical current through the wire will cause the pump chamber to contract to produce a pumping action. Jarvick discloses an electrohydraulic system for total artificial hearts and cardiac assist devices intended for permanent replacement of a human heart or for long-term heart assists. Runge discloses an electrically activated shunt for placement between the left atrium and the descending aorta of a human heart to assist the left ventricle of the heart in pumping blood to the aorta. Robinson et al discloses an implantable hydraulically actuated total cardiac prosthesis.

SUMMARY OF THE INVENTION

The present invention is directed toward providing a pump system and method for pumping fluid from a first location to a second location. The concept of the present invention is to combine a strip of living muscle with a compressable sac that is coupled, for example, to a vein and an artery so that the sac will sequentially contract as the muscle contracts to thereby pump blood from the vein to the artery.

The pump system of the present invention comprises, in general, a chamber means for being associated with first and second locations and for allowing fluid to flow thereinto from the first location; and contraction means for being associated with the chamber means and for causing at least a portion of the chamber means to contract, the contraction means including a length of living muscle for being associated with the chamber means in a manner that contraction of the muscle will cause at least a portion of the chamber to contract.

One object of the present invention is to provide a cardiovascular pump system for being associated with a vein and an artery and which will assist or assume the pumping function of one or both ventricles of a patient's heart.

Another object of the present invention is to provide such a cardiovascular pump system which utilizes a length of living muscle from the patient as means to provide contractive force to cause blood to be pumped from a vein to an artery.

Another object of the present invention is to provide such a cardiovascular pump system which will prevent intermittent collapsing of the vein when blood is drawn into the cardiovascular pump system.

Another object of the present invention is to provide such a cardiovascular pump system which will sequentially stimulate the length of living muscle through multiple stimulation points so as to limit muscle fatigue.

Another object of the present invention is to provide such a cardiovascular pump system which will provide contraction rate and strength so as to produce aortic and/or pulmonary blood pressure and flow similar to that of healthy left and/or right heart ventricles.

Another object of the present invention is to provide such a cardiovascular pump system which will control blood flow as to decreased turbulence.

Another object of the present invention is to provide such a cardiovascular pump system which will fully dilate when the muscle is relaxed.

Another object of the present invention is to provide such a cardiovascular pump system which will reduce cardiac pain, reduce the invasiveness and trauma of cardiovascular surgery while improving the quality of a cardiovascular patient's life.

DESCRIPTION OF THE PREFERRED EMBODIMENT

Figure 1:
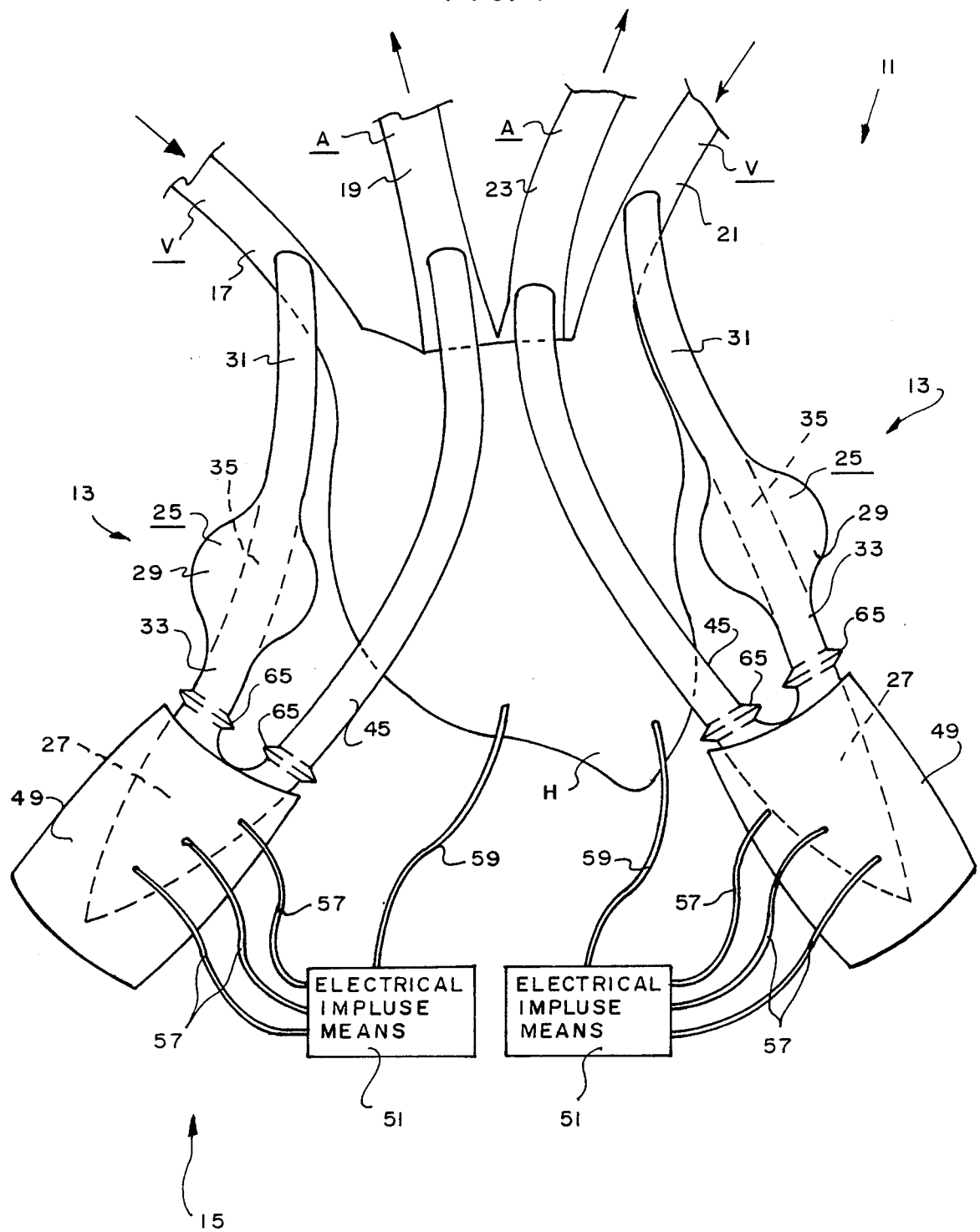
FIG. 1 is a somewhat diagrammatic view of a human heart showing pump systems of the present invention associated with both the left and right ventricles thereof.

The preferred embodiment of the pump system of the present invention is designed as a cardiovascular pump system 11 to assist or assume the pumping functions of a patient's heart H (see FIG. 1). More specifically, the system 11 is designed to pump blood from a first location (i.e., a vein V) to a second location (i.e., an artery A).

The system 11 includes a chamber means 13 for being associated with a vein V and an artery A and for allowing blood to flow thereinto from the vein V; and includes contraction means 15 for being associated with the chamber means 13 and for causing at least a portion of the chamber means 13 to contract to pump blood from a vein V to an artery A.

The system 11 of the present invention may assist or assume the pumping function of either or both the left chamber or ventricle and the right chamber or ventricle of the patient's heart H. Thus, as shown in FIG. 1, the system 11 may include a chamber means 13 and a contraction means 15 for being associated with the left ventricle of the heart H and another chamber means 13 and contraction means 15 for being associated with the right ventricle of the heart H. The chamber means 13 associated with the left ventricle of the heart H pumps blood from the pulmonary vein 17 of the left ventricle of the heart H to the aorta 19 thereof while the chamber means 13 associated with the right ventricle of the heart H pumps blood from a major vein 21 (e.g., the vena cava) of the right ventricle of the heart H to the pulmonary artery 21 thereof as shown in FIG. 1. The basic structure and function of the chamber means 13 and contraction means 15 for either ventricle of the heart H is substantially identical to one another and, therefore, only the chamber means 13 and contraction means 15 shown associated with the left ventricle of the heart H in FIG. 1 will be disclosed in detail. Such a detailed description will enable one of ordinary skill in the art to utilize the system 11 of the present invention with either ventricle of a patient's heart. For clarity, the components and elements of the chamber means 13 and contraction means 15 shown associated with the right ventricle of the heart H in FIG. 1 are identified by the appropriate number herebelow used for the like component or element of the chamber means 13 and contraction means 15 shown or described as associated with the left ventricle of the heart H. It will now be apparent to those of ordinary skill in the art that the optimum design of the various components for assuming or assisting a specific pumping function (e.g., the pumping function of the left or right ventricle of a human heart) will depend upon many variables such as the strength, flow rate, etc. of the specific pumping function to be assumed or assisted, etc.

The chamber means 13 preferably includes a first chamber means 25 for being associated with a vein V for allowing blood to flow thereinto from the vein V and a second chamber means 27 for being associated with the first chamber means 25 and with an artery A for selectively pumping blood from the first chamber means 25 and, therefore, the vein V to the artery A.

The first chamber means 25 preferably includes a somewhat flaccid sac 29 for being coupled to the vein V by an inlet duct 31 and to the second chamber means 27 by an intermediate duct 33. The first chamber means 25 may include internal structure means 35 for preventing or reducing undue strain on the vein V upon collapse of the sac 29. More specifically, the inlet and intermediate ducts 31, 33 may be constructed from a single, unitary length of biocompatible tubing with the sac 29 attached thereabout whereby the portion of the tubing through the sac 29 will define the internal structure means 35 and will prevent or reduce longitudinal movement of the inlet duct 31 toward the first chamber means 25 upon collapse of the sac 29 thereby preventing or reducing movement of the vein V upon collapse of the sac 29. The length of tubing defining the internal structure means 35 has a plurality of apertures 37 therethrough for allowing blood to pass to and from the sac.

The second chamber means 27 preferably includes a sac 39 having an inlet port 41 for being coupled to the intermediate duct 33 to allow blood to pass from the first chamber means 25 through the intermediate duct 33 into the sac 39 and having an outlet port 43 for being coupled to the artery A by an outlet duct 45.

Figure 2:
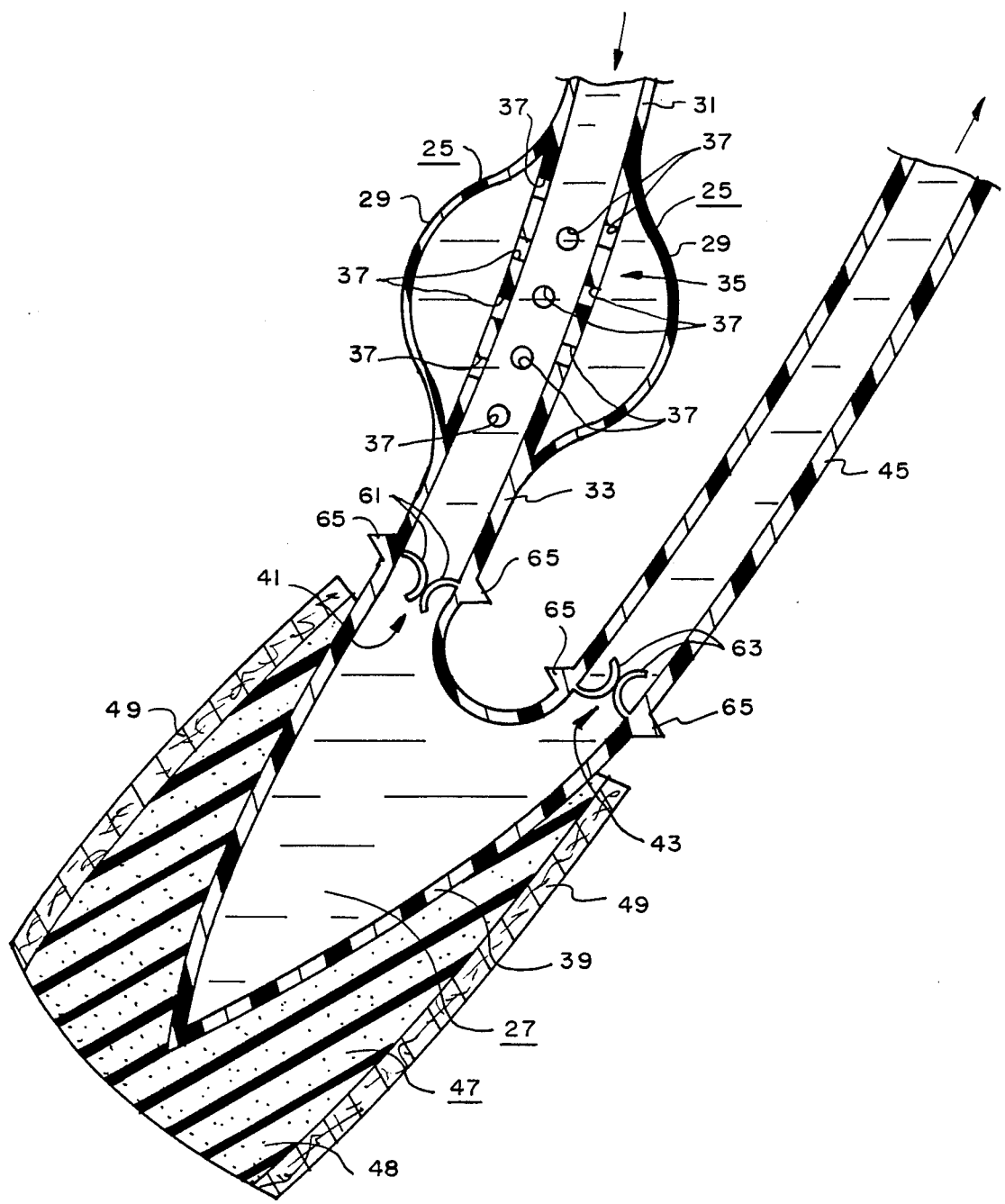
FIG. 2 is a somewhat sectional view of a portion of the pump system of the present invention showing a second chamber in a fully dilated position and showing a first chamber substantially filled.
Figure 3:
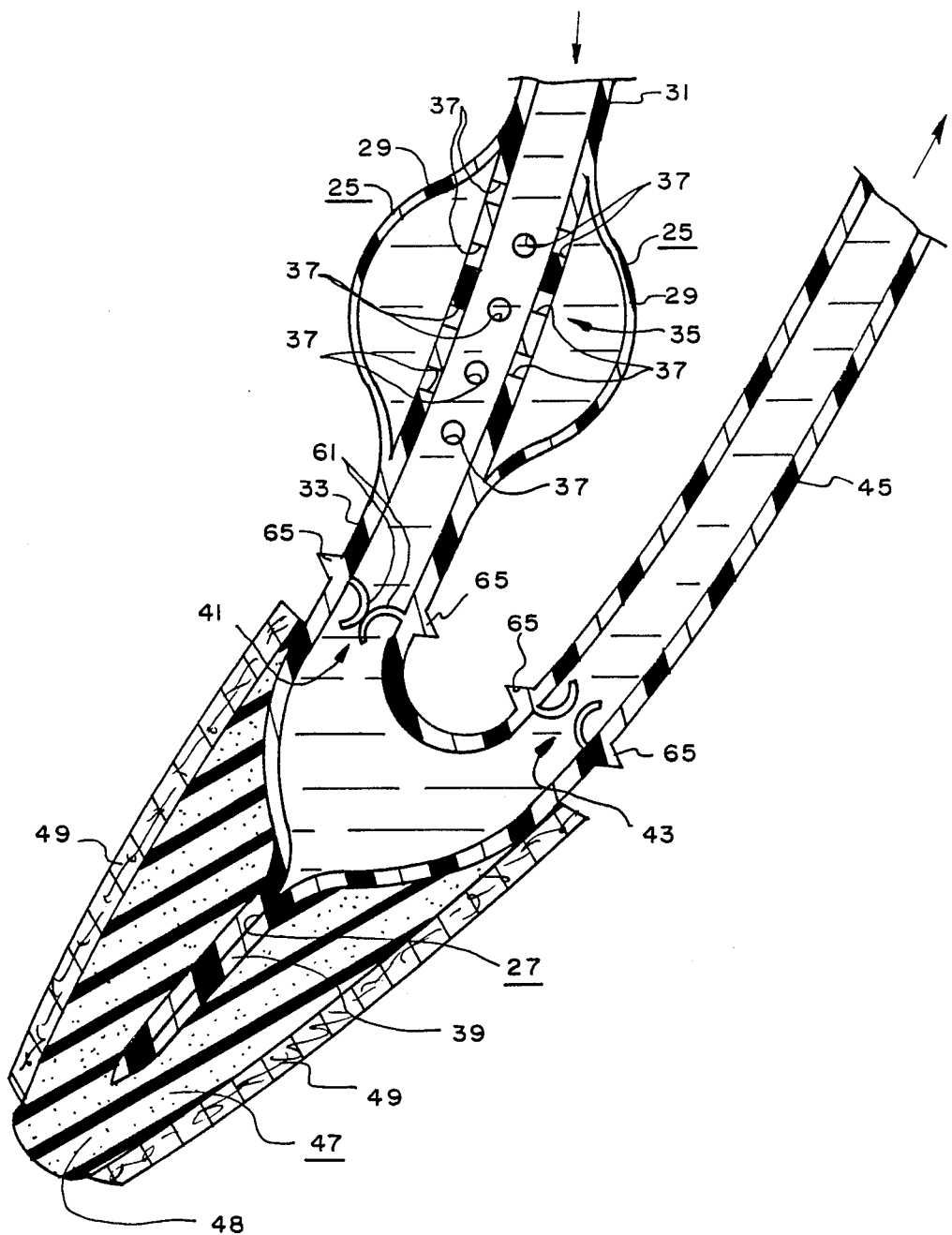
FIG. 3 is a sectional view similar to FIG. 2 but showing the second chamber in a contracted position and showing the first chamber substantially full.
Figure 4:
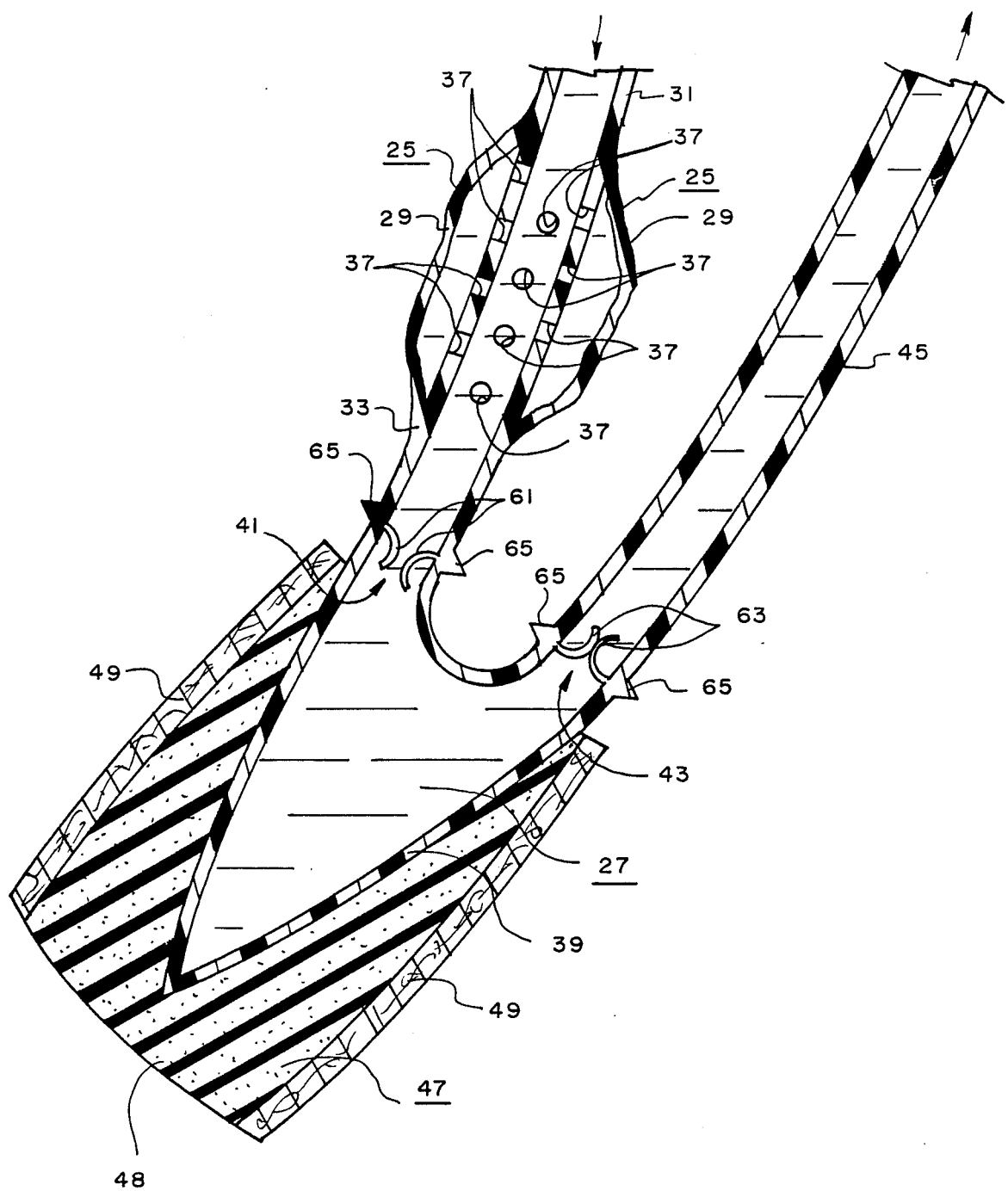
FIG. 4 is a sectional view similar to FIG. 2 but showing the second chamber dilating and showing the first chamber collapsing.
Figure 5:
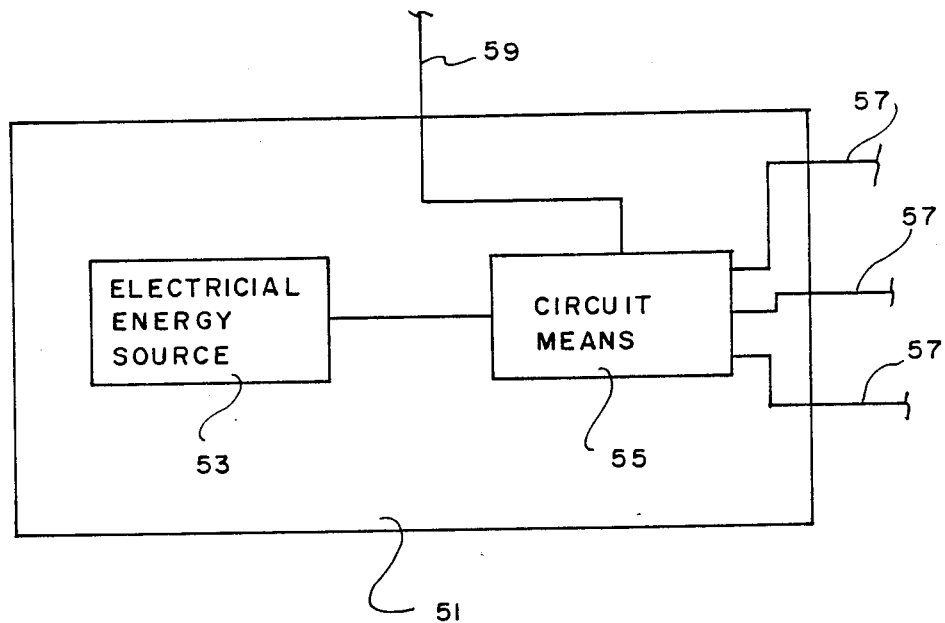
FIG. 5 is a block diagram of the muscle stimulation means.

The second chamber means 27 preferably includes dilation means 47 for causing dilation of the sac 39 when the contraction means 15 is relaxed. Thus, the sac 39 is movable between a dilated position as shown in FIG. 2 and a collapsed position as shown in FIG. 3. The dilation means 47 may consist of a body 48 biocompatible foam secured to the outer surface of the sac 39 in such a manner so as to normally urge the sac 39 to the dilated position.

The contraction means 15 includes a length of living muscle 49 for being associated with the chamber means 13 in a manner that contraction of the muscle 49 will cause at least a portion of the chamber means 13 to contract. More specifically, the muscle 49 is preferably associated with the second chamber means 27 and is preferably wrapped about and sutured to the dilation means 47. Thus, for example, when the system 11 is being implanted in a patient's body, the muscle 19 may consist of a strip of oblique abdominal muscle partially excised from the patient's abdomen in any manner to maintain the necessary blood supply thereto as will now be apparent to those skilled in the art.

The contraction means 15 preferably includes muscle stimulation means 51 for being associated with the muscle 49 and for sequentially causing the muscle 49 to contract. The muscle stimulation means 51 may be of various specific types now apparent to those skilled in the art. Preferably, the muscle stimulation means 51 includes an electrical energy source 53, such as a battery or the like, a circuit means 55 coupled to the electrical energy source 53 for producing sequential electrical impulses, and electrical lead means 57 for extending from the circuit means 55 to the muscle 49 for conveying the electrical impulses to the muscle 49. The muscle stimulation means 49 may include a sensor lead means 59 for extending from the heart H to the circuit means 55 for providing the circuit means 55 with sequential sensory signals from the heart H. The circuit means 55 may include a programmed computer chip or the like for controlling the stimulation of the muscle 49 to produce the desired contraction rate and intensity as will now be apparent to those skilled in the art. The electrical lead means 57 are preferably implanted at various motor points on the muscle 49 to facilitate area sequencing of the muscle 49 to limit fatigue. The muscle stimulation means 51 may, therefore, consist of a typical "pacemaker" or the like adapted to provide specific electrical impulses to a muscle and may be of the type which is "triggered" by signals from a heart or the type is self-controlled, etc., as will now be apparent to those of ordinary skill in the art. While it may be desired to vary the specific signals depending on the pumping function to be performed by the system 11, the construction and operation of muscle stimulation means 51 will now be apparent to those skilled in the art.

The system 11 preferably includes valve means for controlling the direction of blood flow through the chamber means 13. Preferably, the system 11 includes an inlet valve means 61 located adjacent the inlet port 41 of the sac 39 for allowing blood to flow into the sac 39 from the vein V while preventing blood from being pumped from the sac 29 to the vein V. Additionally, the system 11 preferably includes an outlet valve means 63 located adjacent the outlet port 43 of the sac 39 for allowing blood to flow from the sac 39 to the artery A while preventing blood from being drawn from the artery A into the sac 39. The specific construction of the valve means 61, 63 may vary as will now be apparent to those skilled in the art. Thus, for example, the valve means 61, 63 may consist of simple flap valves of any construction and operation well known to those skilled in the art. Means may be provided for preventing the collapse of the valve means 61, 63 when the sac 39 is contracted. Thus, for example, the walls of the intermediate duct 33 and the outer duct 45 adjacent the inlet and outlet ports 41, 43 (and, therefore, adjacent the valve means 61, 63) respectively may be thickened as indicated at 65 so as to prevent or hinder the collapse of the inlet and outlet ports 41, 43 upon contraction of the sac 39.

The various ducts 31, 33, 45; chambers 25, 27 and valves 61, 63 may be constructed out of various biocompatible materials such as silicone rubber or the like in any manner now apparent to those skilled in the art as by being molded or cast. The various angles, curves and the like of the various elements should be contoured so as to reduce turbulence, etc., as blood flows therethrough.

To utilize the system 11 to assist or assume the pumping function of the left and/or right ventricles of the heart H, the distal end of the inlet duct 31 is sutured or otherwise attached to the appropriate vein V in a manner which allows blood to flow from the vein into the duct 31, and the distal end of the outlet duct 45 is sutured or otherwise attached to the appropriate artery A in a manner which allows blood to be pumped from the duct 45 into the artery A. The muscle 49 is partially excised from the patient's abdomen or the like in a manner to maintain the necessary blood supply thereto and is then wrapped about the sac 39 and sutured or otherwise attached thereto in a manner so that contraction of the muscle 49 will cause the sac 39 to contract. The electrical lead means 57 of the muscle stimulation means 51 are implanted within the muscle 49 at various motor points thereof in any manner which will now be apparent to those skilled in the art. The sensor lead means 59 of the muscle stimulation means 51 may be implanted in the appropriate ventricle of the heart H. The muscle stimulation means 51 will sequentially "trigger" the muscle 49 to cause the muscle 49 to sequentially contract the second chamber 27 whereby the system 11 will then assist or assume the pumping function of the appropriate ventricle of the heart H.

Various specific design features of the system 11 may be modified as will now be apparent to those skilled in the art to provide the desired volume and pressure of blood flow to decrease turbulence, etc.

Although the invention has been described and illustrated with respect to a preferred embodiment thereof and a preferred use therefor, it is not to be so limited since changes and modifications can be made therein which are within the full intended scope of the invention.

I claim:

1. A cardiovascular pump system for pumping blood from a vein to an artery said system comprising:
   (a) chamber means for being associated with said vein and said artery and for allowing blood to pass thereinto from said vein; said chamber means including a first chamber means for being associated with said vein and for allowing blood to flow thereinto from said vein, and including a second chamber means for being associated with said first chamber means and with said artery and for pumping blood to said artery; said chamber means further comprising dilation means, said dilation means including a body member formed of a biocompatible, elastic material attached to at least a portion of said second chamber means for being positioned between said muscle and said second chamber means for causing dilation of said second chamber means when said muscle is relaxed, and
   (b) contraction means for being associated with said chamber means and for contracting at least a portion of said second chamber means to pump blood from said second chamber means to said artery, said contraction means including a length of living muscle for being associated with said second chamber means in a manner that contraction of said muscle will cause at least a portion of said second chamber means to contract.

2. The system of claim 1 in which said contraction means includes muscle stimulation means for being associated with said muscle for sequentially causing said muscle to contract.

3. The system of claim 2 in which said muscle stimulation means includes an electrical energy source, a circuit means coupled to said electrical energy source for producing sequential electrical impulses, and electrical lead means for extending from said circuit means to said muscle for conveying said electrical impulses to said muscle.

4. The system of claim 3 in which said pump is for being implanted in a person's body to supplement a ventricle of the person's heart, and in which said muscle stimulation means includes a sensor lead means for extending from said heart to said circuit means for providing said circuit means with sequential sensory signals from said heart.

5. The system of claim 1 in which is included valve means for controlling the direction of blood flow through said chamber means.

6. The system of claim 5 in which said valve means includes a first valve means for controlling the direction of blood flow from said first chamber means to said second chamber means, and includes a second valve means for controlling the direction of blood flow from said second chamber means to said artery.

7. The system of claim 1 in which said first chamber means includes a flaccid, slow-filling sac for accepting venous blood for subsequent filling of said second chamber means and for preventing active suction of said second chamber means from intermittently collapsing said vein.

8. The system of claim 7 in which said first chamber means includes means for preventing longitudinal collapses of said sac, while allowing axial collapse of said sac and for averting strain from being applied to said vein as blood is pumped to said artery.

* * * * *